(12) United States Patent
Parodi

(10) Patent No.: US 6,827,726 B2
(45) Date of Patent: Dec. 7, 2004

(54) INTRODUCER FOR DEPLOYMENT OF BRANCHED PROSTHESIS

(75) Inventor: Juan Carlos Parodi, Buenos Aires (AR)

(73) Assignee: Boston Scientific Corporation, Natick, MA (US)

( * ) Notice: Subject to any disclaimer, the term of this patent is extended or adjusted under 35 U.S.C. 154(b) by 245 days.

(21) Appl. No.: 10/052,197

(22) Filed: Jan. 18, 2002

(65) Prior Publication Data

US 2002/0143383 A1 Oct. 3, 2002

Related U.S. Application Data

(60) Provisional application No. 60/262,787, filed on Jan. 19, 2001.

(51) Int. Cl.$^7$ ............................................. A61M 29/00
(52) U.S. Cl. ...................................................... 606/194
(58) Field of Search ....................... 623/1, 11; 606/108, 606/194; 604/912, 170.01

(56) References Cited

U.S. PATENT DOCUMENTS

| | | | |
|---|---|---|---|
| 4,552,554 A | 11/1985 | Gould et al. ................... | 604/51 |
| 4,905,667 A | 3/1990 | Foerster et al. ................. | 128/4 |
| 4,931,039 A | 6/1990 | Coe et al. ...................... | 604/53 |
| 5,984,955 A | 11/1999 | Wisselink ....................... | 623/1 |
| 6,022,342 A | 2/2000 | Zmukherjee ................ | 604/523 |

FOREIGN PATENT DOCUMENTS

| | | |
|---|---|---|
| EP | 1 031 328 | 8/2000 |
| WO | WO 98/16174 | 4/1998 |
| WO | WO 99/25280 | 5/1999 |
| WO | WO 99/47078 | 9/1999 |

*Primary Examiner*—David O. Reip
*Assistant Examiner*—Bradford C Pantuck
(74) *Attorney, Agent, or Firm*—RatnerPrestia

(57) ABSTRACT

An introducer for implanting a prosthesis in a junction of a main lumen and a branch lumen. The prosthesis comprises a trunk to be implanted within the main lumen and at least one arm to be implanted within the branch lumen. The introducer comprises an outer sheath, an axial guide wire and at least one peripheral guide wire slideable within the outer sheath, and a nose cone at a distal end of the sheath. The nose cone has an axial conduit for receiving the axial guide wire and at least one peripheral channel for guiding the peripheral guide wire and guiding it into the branch lumen. A unitary branched prosthesis having at least one radial arm may be deployed using this introducer. Methods for deploying a unitary or modular branched prosthesis at a junction in a lumen use the introducer of this invention.

31 Claims, 4 Drawing Sheets

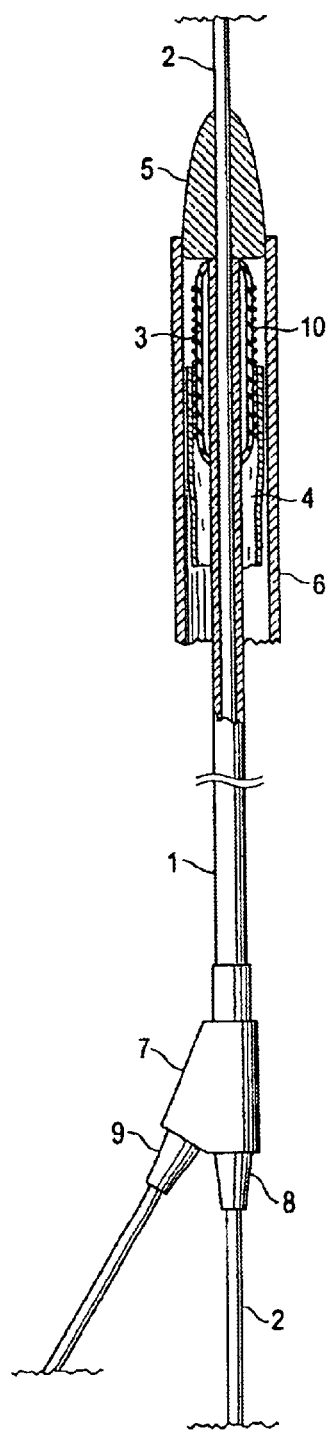
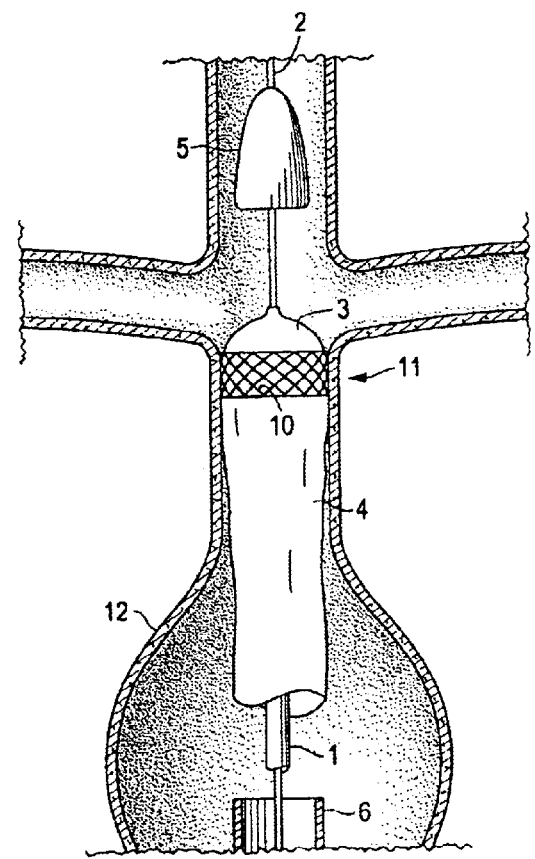
FIG. 1
PRIOR ART
FIG. 2
PRIOR ART

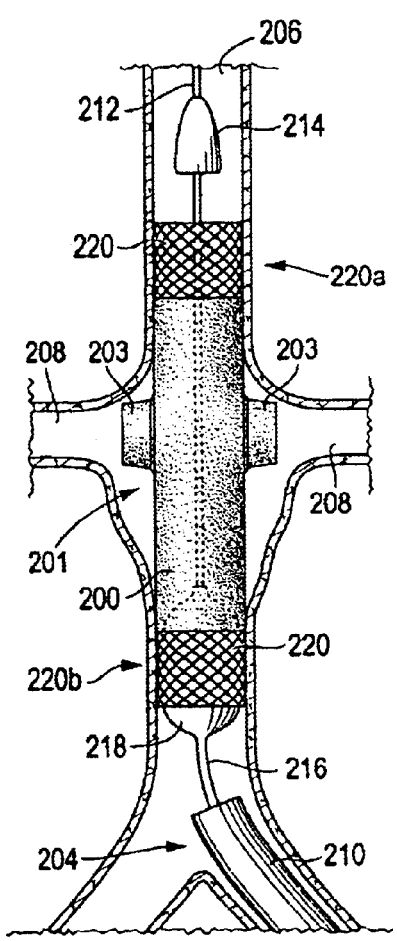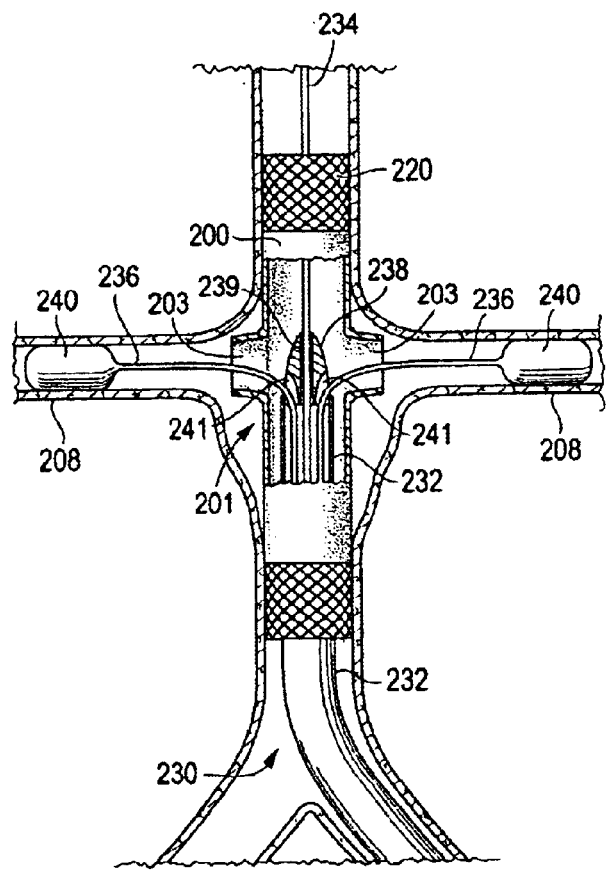
FIG. 8A     FIG. 8B
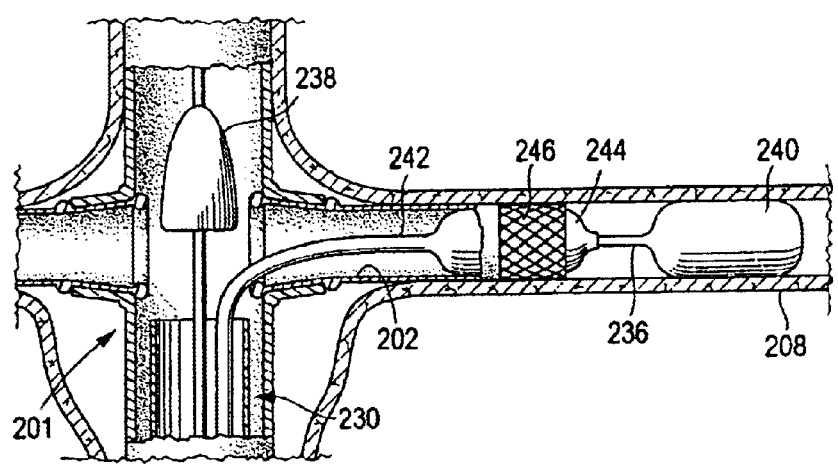
FIG. 8C

INTRODUCER FOR DEPLOYMENT OF BRANCHED PROSTHESIS

CROSS-REFERENCE TO RELATED APPLICATION

This application claims priority of U.S. Provisional Application No. 60/262,787, filed Jan. 19, 2001.

TECHNICAL FIELD

The present invention relates to an introducer and method for treating a branched lumen and more particularly, an introducer and method for implanting an intraluminal prosthesis having a trunk and at least one arm into a branched lumen, such as the aorta and the renal arteries.

BACKGROUND OF THE INVENTION

Introducers for implanting prostheses or grafts, such as for repairing aneurysms, are well known for medical practitioners. These introducers essentially comprise a catheter with an inflatable balloon at a distal end thereof. The graft is typically wrapped over the deflated balloon and the catheter-prosthesis assembly is disposed within an outer sheath for insertion into a blood vessel. The introducer is moved along the vessel until positioned in a desired location in a portion of the vessel to be repaired. Once in position, the sheath is retracted to expose the graft-balloon assembly and the balloon is inflated by pressurizing the catheter with fluid. During inflation of the balloon, the prosthesis is expanded and implanted in the vessel wall. The implantation is facilitated by use of intravascular devices called "stents." A stent is a mechanical scaffolding that is typically sutured to the graft and that is expanded, for example by deformation from a compressed diameter to an expanded diameter by inflation of the balloon. The stent, once in its expanded shape against the internal side of the blood vessel, is resistant to compression and therefore holds the graft in place.

Many prostheses known in the art are implanted by means of an introducer having an elongated balloon or a pair of balloons each located at respective ends of the cylindrical prosthesis. Others comprise two or more portions that must be assembled inside the blood vessel, for example to repair a bifurcated length of the vessel, such as the bifurcation of the aorta into the iliac arteries. So-called "modular" grafts comprising two, three, or more portions are typically implanted by installing one portion at a time and connecting the portions to each other while in situ inside the lumen.

FIGS. 1 and 2 show a diagrammatic view of a typical catheter 1 of the prior art. Catheter 1 typically has two lumina extending axially through the catheter: a first lumen (not shown) for sliding the catheter over a guide wire 2, and a second lumen (not shown) concentrically encompassing the first lumen and in fluid communication with a radially-expandable balloon 3. Prosthesis 4 is schematically shown wrapped over balloon 3. Prosthesis 4 comprises one or more stents 10 (shown in FIG. 2) to be expanded against a vessel wall for implantation. The catheter-prosthesis assembly is mounted within sheath 6. Nose cone 5 is provided at a distal end of the introducer. The purpose of the nose cone is to provide a smooth, soft tip for preventing injury to the blood vessel as the introducer is manipulated and pushed through the body lumen to reach the desired location. Nose cone 5 also closes off the distal end of the introducer to prevent blood from entering into the introducer.

At the proximal end of the introducer, the first and second lumen branch out at angular piece 7 forming an outlet 8 for wire 2 and a connection line 9 connected to a valve (not shown) for supplying the pressurized fluid into the second lumen for inflating the balloon.

FIG. 2 shows introducer 1 after having been moved along lumen 12 until reaching a deployment location, such as an aortic aneurysm. Balloon 3 is inflated to exert a radial expanding force from inside prosthesis 4 to radially deform stent 10 until it is implanted against the interior side of a distal portion 11 of lumen 12, such as an upper neck of an aorta affected by an aneurysm. Guide wire 2 serves to guide the insertion of introducer 1 as well as to assist in positioning graft 4 and stent 10 in the desired location for inflating balloon 3.

There are, however, situations where a vessel has, in a section thereof, a junction with one or more branch vessels, such as the junction between the aorta and the renal arteries. A graft for implantation at such a junction, such as for repairing a disorder at the junction of the aorta and renal arteries, requires a different introducer and different deployment method, as a branched graft cannot be implanted without being able to access the aorta and the renal arteries simultaneously to connect the several portions together. Thus, the introducer shown in FIGS. 1 and 2 would be inadequate for such an implantation, as the complex shape of the necessary prosthesis requires multiple guide wires, and any maneuver to attempt to implant such a complex graft using this introducer would be tedious, difficult, complex and time consuming, if not impossible.

Therefore, there is a need in the art to provide an introducer and implantation method for implanting a modular or unitary graft into a branched lumen, such as at the junction of the aorta and renal arteries, by a simple, easy and safe way, taking only reasonable time for the safety of the patient.

SUMMARY OF THE INVENTION

The various features and advantages of this invention are better understood when taken in connection with the accompanying drawings and description. The present invention comprises an introducer for insertion in a lumen from a proximal location outside the lumen to a distal location within the lumen for deployment of a prosthesis at a junction of a main lumen and at least one branch lumen. The introducer comprises an outer sheath having a distal end, an axial guide wire slidable within the outer sheath, at least one peripheral guide wire slidable within the outer sheath, and a nose cone located at the distal end of the outer sheath. The nose cone has a periphery, an axial conduit slidable over the axial guide wire, and at least one peripheral channel spaced apart from the axial conduit for receiving one of the peripheral guide wires. Each peripheral channel may be open to the periphery of the nose cone and may provide communication between an interior of the introducer and the lumen when the nose cone is positioned at the distal end of the sheath. Each peripheral guide wire may comprise an expandable balloon at its distal end.

The introducer may further comprise a trunk deployment catheter and at least one peripheral deployment catheter. The trunk deployment catheter is concentric with the axial guide wire and has at least one inflatable deployment balloon at its distal end. Each peripheral deployment catheter is concentric with one of the peripheral guide wires and has at least one inflatable deployment balloon at its distal end.

The invention also comprises a nose cone for use with an introducer for insertion of a prosthesis in a lumen. The nose cone defines an axial conduit for receiving a first guide wire and at least one peripheral channel spaced apart from the axial conduit for receiving a second guide wire. The nose cone typically has a periphery and each peripheral channel is open to the periphery of the nose cone. The nose cone may comprise two peripheral channels that may be diametrically opposed.

The invention also comprises a unitary prosthesis for deployment in a distal location positioned at a junction of a main lumen and at least one branch lumen. The prosthesis comprises a trunk section and at least one arm section extending radially from the trunk section. The arm section may be approximately perpendicular to the trunk section. The unitary prosthesis may comprise two arm sections, such as for deployment at the junction between the aorta and the renal arteries.

The unitary prosthesis may comprise a graft and at least one stent. The stent may comprise a distal trunk stent portion expandable for deployment in a distal portion of the main lumen distal the branch lumen, a proximal trunk stent portion expandable for deployment in a proximal portion of the main lumen proximal the branch lumen, and at least one branch stent portion expandable for deployment in one of the branch lumen. The distal trunk stent portion, the proximal trunk stent portion, and each branch stent portion may each comprise separate stents.

The invention also comprises a method for implanting a unitary prosthesis in a distal location at a junction of a main lumen and at least one branch lumen. The prosthesis to be implanted comprises at least one stent and has a trunk for implantation into the main lumen and at least one arm for implantation into the branch lumen. The method comprises providing an introducer comprising an outer sheath, an axial guide wire and at least one peripheral guide wire slidable within the outer sheath, a nose cone at a distal end of the outer sheath, a trunk deployment catheter concentric with the axial guidewire and having at least one inflatable deployment balloon, and at least one arm deployment catheter concentric with the peripheral guide wire and having at least one inflatable deployment balloon. The nose cone has an axial conduit slidable over the axial guide wire and at least one peripheral guide channel each for receiving one of the peripheral guide wires. Each peripheral guide wire comprises an inflatable anchor balloon at its distal end. The prosthesis is provided inside the outer sheath with the trunk mounted over the axial guide wire and at least one trunk stent portion mounted over each inflatable deployment balloon of the trunk deployment catheter. Each arm is mounted over one of the peripheral guide wires and at least one arm stent portion is mounted over each inflatable deployment balloon of each arm deployment catheter.

The introducer is fed into the lumen until reaching an implantation position adjacent the branch lumen. The introducer is maintained in the implantation position while advancing each peripheral guide wire distally through one of the peripheral channels of the nose cone until each wire is positioned at a sufficient depth within the corresponding branch lumen. Each anchor balloon on each peripheral guide wire is then inflated to fix the wire in a set position, and the prosthesis is advanced over the axial and peripheral guide wires until each arm of the prosthesis is positioned at a sufficient depth within the branch lumen. Then, the deployment balloons are inflated to expand at least the trunk and arm stent portions of the prosthesis to implant the prosthesis. The method may be used to repair an aneurysm.

The invention also comprises a method for implanting a modular prosthesis comprising a trunk module for implantation into the main lumen and at least one arm module for implantation into the branch lumen. The trunk module comprises at least one stent and at least one arm fitting. The arm module is adapted to interconnect with the arm fitting of the trunk module and comprises at least one stent.

The method initially comprises introducing a first introducer into the main lumen until reaching a first implantation position adjacent the branch lumen. The first introducer comprises an outer sheath, an axial guide wire slidable within the outer sheath, a nose cone at a distal end of the outer sheath, and a trunk deployment catheter. The nose cone has an axial conduit slidable over the axial guide wire. The trunk deployment catheter is concentric with the axial guidewire and has at least one inflatable deployment balloon. The modular prosthesis is mounted inside the outer sheath with the trunk module mounted over the axial guide wire and at least one trunk stent portion mounted over each inflatable deployment balloon of the trunk deployment catheter.

The nose cone is advanced distally to a location distal of the junction of the main lumen with the branch lumen and the trunk module is implanted with each arm fitting aligned with a corresponding branch lumen. The trunk section deployment balloons are inflated to expand the trunk stent portions. Then, a second introducer is introduced into the lumen to a second implantation position. The second introducer comprises an outer sheath, an axial guide wire and at least one peripheral guide wire slidable within the outer sheath, a nose cone at a distal end of the outer sheath, a trunk deployment catheter concentric with the axial guidewire and having at least one inflatable deployment balloon, and at least one arm deployment catheter concentric with the peripheral guide wire and having at least one inflatable deployment balloon. The nose cone has an axial conduit slidable over the axial guide wire and at least one peripheral guide channel each for receiving one of the peripheral guide wires. Each peripheral wire comprises an inflatable anchor balloon at a distal end thereof. Each arm module is mounted over one of the peripheral guide wires and at least one arm stent portion of each arm module is mounted over each inflatable deployment balloon of each arm deployment catheter.

The second introducer is maintained in the implantation position while advancing each peripheral guide wire distally through one of the peripheral channels of the nose cone and through one of the arm fittings in the implanted trunk module until each peripheral guide wire is positioned at a sufficient depth within the corresponding branch lumen. Then, each anchor balloon on each peripheral guide wire is inflated to fix the wire in a set position. Each arm module is then advanced over one of the peripheral guide wires until each arm module is positioned at a sufficient depth within the branch lumen and in an interlocking position with one of the arm fittings of the trunk module. Finally, each arm deployment balloon is inflated to expand at least the arm stent portions of each arm module to implant the arm module within the branch lumen and within the corresponding arm fitting of the trunk module.

The invention also comprises a method for implanting at a junction of a main lumen and at least one branch lumen, a prosthesis comprising at least one portion for implantation into the branch lumen. The method comprises the steps of providing an introducer comprising an outer sheath, an axial guide wire and at least one peripheral guide wire slidable within the outer sheath, and a nose cone at a distal end of the outer sheath. The nose cone has an axial conduit slidable over the axial guide wire and at least one peripheral guide channel for receiving the peripheral guide wire. The peripheral wire comprises an inflatable anchor balloon at its distal end. The introducer is introduced into the lumen until reaching an implantation position adjacent the branch lumen. The introducer is maintained in the implantation position while advancing the peripheral guide wire distally through the peripheral channel of the nose cone until the wire is positioned at a sufficient depth the branch lumen. Then, the anchor balloon is inflated to fix the peripheral guide wire in a set position. The prosthesis is advanced over the peripheral guide wire until at least a portion of the prosthesis is positioned at a sufficient depth within the branch lumen, and then at least a portion of the prosthesis is expanded, such as by balloon expansion, for implantation in the branch lumen.

BRIEF DESCRIPTION OF THE DRAWINGS

The present invention is illustrated by way of example in the following drawings wherein:

FIG. 1 shows a partial cross-sectional view of a catheter of the prior art with a nose cone at the distal end of the catheter;

FIG. 2 shows a cross-sectional view of an aortic cylindrical prosthesis being implanted using by the catheter of FIG. 1;

FIG. 8A shows a cross-sectional view of the junction of the aorta and the renal arteries with a trunk module implanted therein, illustrating an exemplary method of this invention for deployment of a modular prosthesis.

FIG. 8B shows the cross-sectional view of FIG. 8A, further showing a partial cross-section of the trunk module and the peripheral guide wire deployment step.

FIG. 8C shows a partial view of the cross-section of FIG. 8B, showing a partial cross section of an arm module during a deployment step.

DESCRIPTION OF THE PREFERRED EMBODIMENTS

Figure 3:
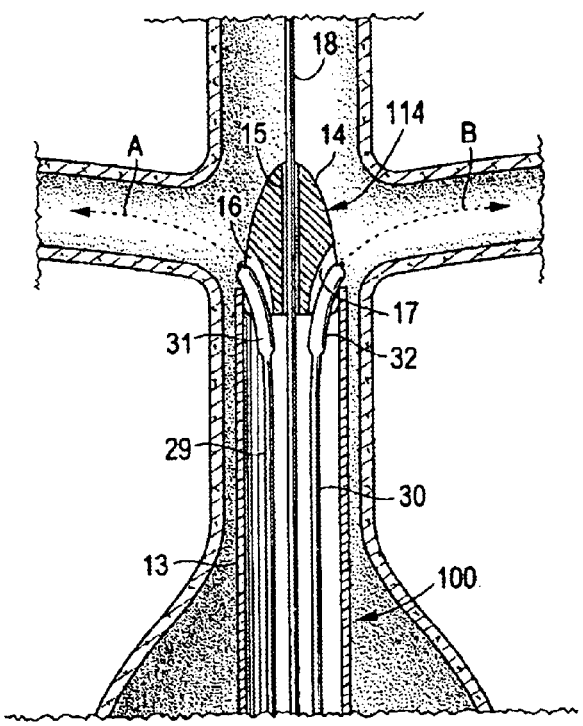
FIG. 3 shows a cross-sectional view of a distal end of an exemplary introducer according to the present invention, showing the nose cone and three guide wires.

Referring now to FIGS. 2–7, there is shown an exemplary introducer and prosthesis of the invention. Introducer 100 comprises a sheath 13 having a novel nose cone 14 located at a distal end of the introducer. The nose cone has an axial conduit 15 for receiving an axial guide wire 18 and one or more peripheral channels 16 and 17, spaced apart from each other and from the central orifice. Axial conduit 15 is shown centrally located and channels 16 and 17 diametrically opposed, but the positions of the conduit and channels may be in any configuration advantageous to deploy a prosthesis of a desired geometry in a junction of at least two lumen.

Nose cone 14 serves many of the purposes of standard nose cones known in the art, but also provides additional structure to guide multiple guide wires.

Because of the multiple wires within sheath 13, introducer 100 may implant a prosthesis having multiple portions or complex configurations. Thus, for repairing a portion of a lumen at a junction with at least one other lumen, such as the junction of the aorta and the renal arteries for example, a more complex graft, like the one shown in FIG. 5, may be implanted.

Figure 4:
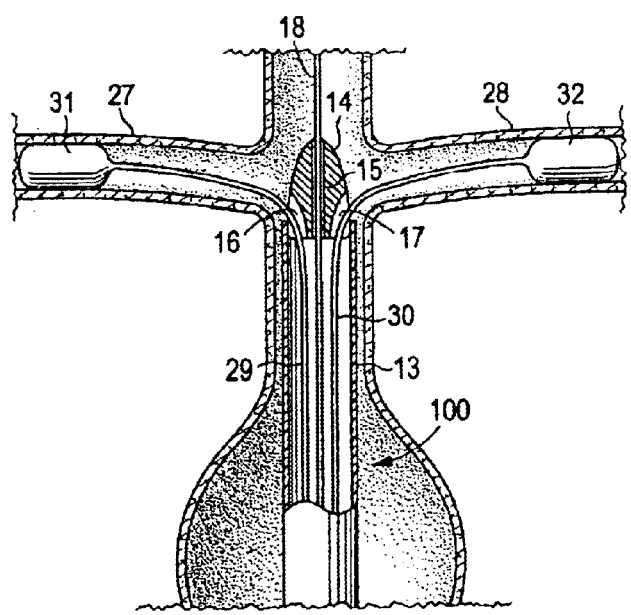
FIG. 4 shows a cross-sectional view of the introducer of FIG. 3, showing the peripheral guide wires anchored within the renal arteries by inflated anchor balloons.
Figure 5:
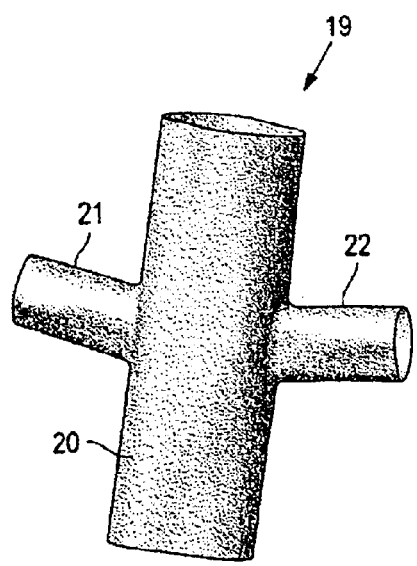
FIG. 5 shows a perspective view of an exemplary graft of this invention having a trunk and two arms for implanting at a junction of lumen such as the aorta and the renal arteries.
Figure 7:
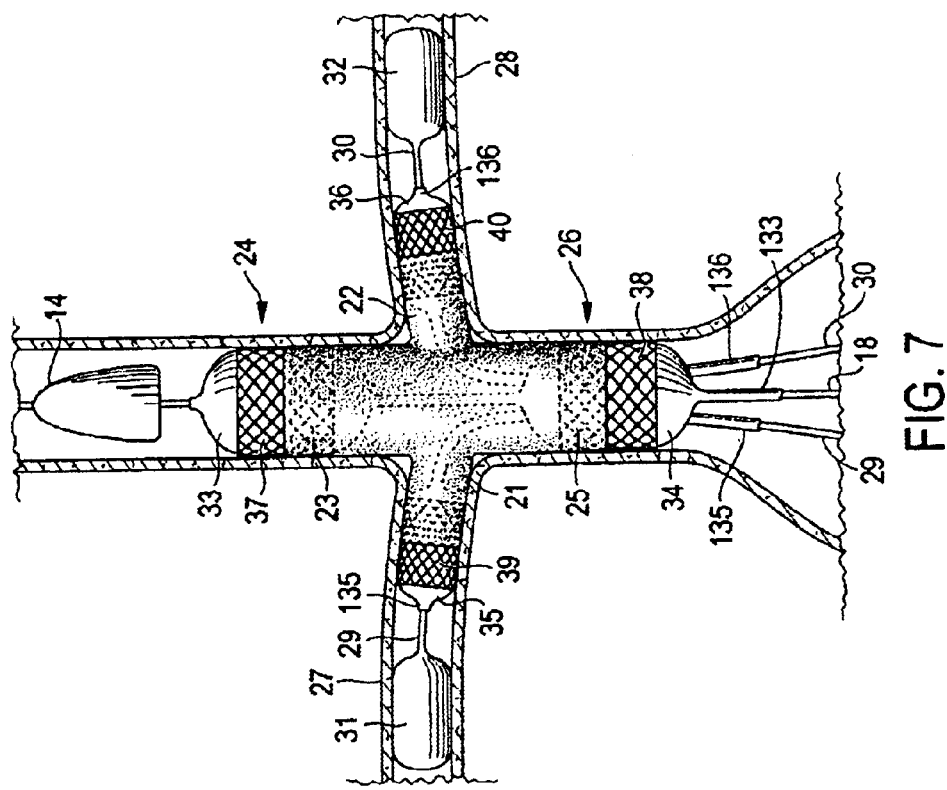
FIG. 7 shows a cross-sectional view of the junction of the aorta and the renal arteries with the graft of FIG. 5 implanted therein with the deployment and anchor balloons inflated.

A prosthesis like the one shown in FIG. 5 may be successfully and easily implanted in a simple operation using the exemplary introducer shown in FIGS. 3, 4, 6, and 7. Graft 19, as shown in FIG. 5, comprises a trunk 20 and two arms 21 and 22. The trunk is adapted for implantation into a main lumen, such as the aorta, and arms 21 and 22 are adapted for implantation into respective branch lumen, such as the renal arteries. More precisely, as shown in FIG. 7, trunk 20 has a distal end 23 for implantation in a distal portion 24 of the aorta distal of renal arteries 27 and 28, and a proximal end 25 for implantation in a proximal portion 26 of the aorta proximal of the renal arteries. Arms 21 and 22 are implanted into renal arteries 27 and 28, respectively.

Before implanting prosthesis 19, sheath 13 is located at the position shown in FIG. 4 and peripheral guide wires 29 and 30 are advanced out of sheath 13 into renal arteries 27 and 28 along respective paths shown by dashed arrows A and B in FIG. 3. This movement is facilitated and guided by the curved design of channels 16 and 17 of nose cone 14. Channels 16 and 17 are preferably open to the outer periphery 114 of nose cone 14, as shown in FIG. 3. Peripheral guide wires 29 and 30 have, at their distal ends, respective inflatable anchor balloons 31 and 32, shown in an uninflated configuration in FIG. 3. As shown in FIG. 4, once in position within the respective renal arteries 27 and 28, anchor balloons 31 and 32 are inflated to anchor wires 29 and 30, respectively, within the arteries.

Figure 6:
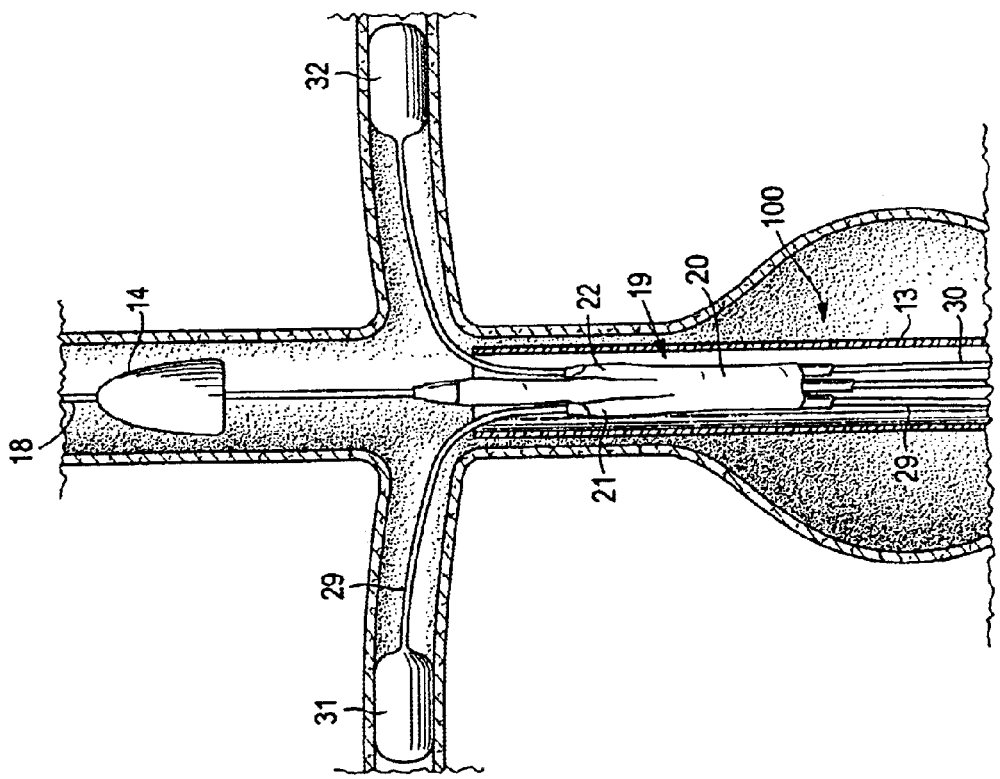
FIG. 6 shows a cross-sectional view of the introducer of FIG. 4 with the graft of FIG. 5 mounted on the guide wires.

FIG. 6 shows graft 19 mounted over wires 18, 29, and 30 with trunk 20 running over wire 18 and arms 21 and 22 running over wires 29 and 30, respectively. The trunk is mounted over distal and proximal deployment balloons 33 and 34, respectively, and each arm 21 and 22 is mounted over corresponding deployment balloon 35 and 36. Deployment balloons 33 and 34 are a part of trunk deployment catheter 133 and deployment balloons 35 and 36 are each a part of distinct arm deployment catheters 135 and 136, respectively. Deployment balloons 33–36 are then inflated to implant the respective parts of the graft within the aorta and the renal arteries, as shown in FIG. 7. The graft is implanted by expanding distal stent 37 and proximal stent 38, located in the distal and proximal ends of the trunk respectively, and left renal stent 39 and right renal stent 40, located in left and right arms 21 and 22, respectively.

According to the method of the invention, the introducer carrying the prosthesis 19 is located such that arms 21 and 22 enter respective renal arteries 27 and 28. The arms are easily guided by peripheral guide wires 29 and 30 because the peripheral guide wires are firmly retained by anchor balloons 31 and 32, respectively. Once in position, balloons 33, 35, and 36 are inflated, simultaneously or in any sequence desired, to implant the distal end of trunk 20 and arms 21 and 22. Balloon 34 may also be inflated at any time, but it is preferable to deflate balloons 33, 35, and 36 and remove wires 18, 29 and 30 out of trunk 20 first before inflating balloon 34 to implant stent 38. In an alternative embodiment without balloon 34, stent 38 may be implanted by balloon 33 after stent 37 has been implanted, by retracting wire 18 proximally until balloon 33 is in position to expand stent 38. Thus, a single balloon 33 may enough to implanting both the distal and proximal portions of trunk 20 within the aorta.

In summary, an exemplary deployment method of the invention comprises introducing the introducer into the lumen until reaching a deployment position adjacent a junction of a main lumen and one or more branch lumen, such as the junction among aorta 12 and renal arteries 27 and 28. The introducer is retained in the deployment position while advancing peripheral guide wires 29 and 30 distally through peripheral channels 16 and 17 of nose cone 14, until each wire enters the corresponding renal artery. Anchor balloons 31 and 32 are then inflated to fix peripheral guide wires 29 and 30 wires in position within the renal arteries. Prosthesis 19 is then advanced over guide wires 18, 29 and 30 using deployment catheters 133, 135, and 136 until arms 21 and 22 of the prosthesis are positioned within the renal arteries. Deployment balloons 33–36 are then inflated inside prosthesis 19 to expand stents 37–40 to implant the trunk and the arms of the prosthesis where desired. Inflation of balloons 33–36 may be carried out simultaneously or sequentially to effect adequate installation.

Although the introducer described herein is useful for deploying a unitary branched prosthesis as shown in FIG. 5, modular branched prostheses are known in the art, such as are described in U.S. Pat. No. 5,984,955, which is incorporated herein by reference. The elements of the present invention are also advantageous for deploying a modular prosthesis 201 comprising a trunk module 200 and at least one arm module 202, as shown in FIGS. 8A–8C. Trunk module 200 has at least one arm fitting 203 into which arm module 202 interlocks.

The modular prosthesis deployment method comprises introducing a first introducer 204 into main lumen 206 until reaching an implantation position adjacent branch lumen 208, as shown in FIG. 8A. First introducer 204 comprises at least outer sheath 210, axial guide wire 212, a nose cone 214 having at least an axial conduit slidable over the axial guide wire. First introducer 204 also comprises a trunk deployment catheter 216 concentric with axial guidewire 212 and having at least one inflatable deployment balloon 218. For introduction, modular prosthesis 201 is compressed inside outer sheath 210 with trunk module 200 mounted over axial guide wire 212 and at least one trunk stent portion 220 mounted over each inflatable deployment balloon 218 of the trunk deployment catheter 216.

To deploy trunk module 200, nose cone 214 is first advanced distally to a location distal of the junction of main lumen 206 with the branch lumen 208. Then, trunk module 200 is implanted with each arm fitting 203 aligned with a corresponding branch lumen 208 by inflating the trunk section deployment balloons 218 to expand the trunk stent portions 220. A single trunk section deployment balloon 218 may be used to first inflate distal trunk section 220a and then proximal trunk section 220b, as shown in FIG. 8A.

Then, as shown in FIG. 8B, a second introducer 230 is maneuvered into deployment position. Second introducer 230 comprises an outer sheath 232, an axial guide wire 234 and at least one peripheral guide wire 236 slidable within the outer sheath, and a nose cone 238 at a distal end of the outer sheath, the nose cone having an axial conduit 239 slidable over the axial guide wire and a peripheral guide channel 241 for receiving the peripheral guide wire. Each peripheral guide wire comprises an inflatable anchor balloon 240 at its distal end. Second introducer 230 is maintained in the position shown in FIG. 8B while advancing each peripheral guide wire 236 distally through one of peripheral channels 241 of nose cone 238 and through arm fitting 203 in implanted trunk module 200 until each peripheral guide wire 236 is positioned at a sufficient depth within the branch lumen 208. Anchor balloon 240 on each peripheral guide wire 236 is inflated to fix the wire in a set position.

As shown in FIG. 8C, introducer 230 further comprises an arm deployment catheter 242 concentric with peripheral guide wire 236 and having at least one inflatable deployment balloon 244. For introduction into the lumen, arm module 202 is mounted over peripheral guide wire 236 with arm stent portion 246 mounted over inflatable deployment balloon 244. After deployment of peripheral guide wires 236, nose cone 238 is advanced distally out of the way so that each arm module 202 may be advanced over each peripheral guide wire 236 until the arm module is positioned at a sufficient depth within branch lumen 208 and in an interlocking position with arm fittings 203. Arm deployment balloon 244 is then inflated to expand arm stent portion 246 to implant arm module 202 within branch lumen 208 and within arm fitting 203 of trunk module 200. Although shown in FIG. 8C with a "snap fit" between arm module 202 and arm filling 203, any type of fitting may be present, including a stent-reinforced fit. Additional deployment balloons may thus be present for securing the fit at arm fitting 203. Alternatively, deployment balloon 244 may be used to inflate any and all stents in arm module 202, either as a single balloon stretching across the all the stents that are present in the arm module, or by inflating to deploy a first stent, moving the balloon, and then inflating it again to deploy one or more other stents.

Although a single arm module 202 is shown being implanted in one of branch lumen 208 in FIG. 8C, the same steps may be repeated for additional arms. The modular prostheses, like the unitary prosthesis shown and described herein, may comprise a single arm, two arms such as for implantation in the aorta and renal arteries, or more than two arms. As used herein, the word "unitary" means "not modular," in other words, comprising a single unit rather than multiple sections that need assembly either in situ or before implantation.

Although the method above is shown and described using two separate introducers 204 and 230, a single introducer may be used to perform the modular deployment method. In such case, trunk module 200 is deployed with the arm module 202 and arm deployment catheter 242 positioned within outer sheath 210 proximal of the proximal end of the trunk module. After deployment of trunk module 200, nose cone 214 (which has at least one peripheral channel 241) is retracted to the position of nose cone 238 aligned with branch lumen 208 as shown in FIG. 8B. Arm deployment catheter 242 is then advanced distally into the peripheral channel of nose cone 214 and out into branch lumen 208.

Although shown in each embodiment with separate stents for each of the distal and proximal trunk stent portions and each of the arm stent portions, a single continuous stent may be present in the unitary stent embodiment or each module may comprise a single continuous stent throughout that module. Likewise, separate stent portions in addition to those specifically denoted herein may be present. Deployment balloons may therefore be placed and inflated accordingly to deploy the prosthesis as desired.

Although shown with branch lumen 208 perpendicular to main lumen 206, branch lumen may make any angle with the main lumen. Accordingly, the configuration of nose cone channels 14 may be tailored to deflect the peripheral guide wires as needed.

While deployment of a unitary prosthesis lends itself best to using balloon-expandable stents, the nose cone of this invention for directing guide wires into branch lumen is not limited to use only with balloon-expandable stents. Thus, self-expanding stents may also be deployed over guidewires placed using a nose cone with peripheral channels. For example, a modular prosthesis comprising self-expanding stents may be deployed by a method similar to the modular method described herein, except that instead of inflating a balloon to deploy each stent, a sheath or other constraint, such as a crochet-loop, may be released to deploy each stent portion.

While preferred embodiments of the present invention have been illustrated and described, it will be obvious to those skilled in the art that various changes and modifications may be made therein without departing from the scope of the invention as defined in the appended claims.

What is claimed:

1. An introducer for insertion in a lumen from a proximal location outside the lumen to a distal location within the lumen for deployment of a prosthesis at a junction of a main lumen and at least one branch lumen, the introducer comprising:
   an outer sheath having a distal end;
   an axial guide wire slidable within the outer sheath;
   at least one peripheral guide wire slidable within the outer sheath, the peripheral guide wire comprising an expandable balloon at a distal end thereof; and
   a nose cone located at the distal end of the outer sheath, the nose cone having a periphery, an axial conduit slidable over the axial guide wire, and at least one peripheral channel spaced apart from the axial conduit for receiving one of the peripheral guide wires.

2. The introducer of claim 1, wherein each peripheral channel is open to the periphery of the nose cone.

3. The introducer of claim 2, wherein each peripheral channel provides communication between an interior of the introducer and the lumen when the nose cone is positioned at the distal end of the sheath.

4. The introducer of claim 1, wherein the at least one peripheral guide wire comprises two peripheral guide wires and the at least one peripheral channel comprises two peripheral channels, each for receiving one of the peripheral guide wires.

5. The introducer of claim 4, wherein the two peripheral channels are located at diametrically opposed locations on the nose cone.

6. The introducer of claim 1 further comprising:
   a trunk deployment catheter concentric with the axial guide wire and having at least one inflatable deployment balloon at a distal end thereof; and
   at least one peripheral deployment catheter, each concentric with one of the peripheral guide wires and having at least one inflatable deployment balloon at a distal end thereof.

7. The introducer of claim 6 further comprising:
   a prosthesis for deployment in the body lumen, the prosthesis comprising a trunk and at least one arm extending radially from the trunk, the prosthesis adapted to be introduced into the lumen in a compressed configuration with the trunk concentric with the trunk deployment catheter and each arm concentric with one of the peripheral deployment catheters, the prosthesis adapted to be deployed in the lumen in an expanded configuration with the trunk in the main lumen and each arm in one of the branch lumen.

8. The introducer of claim 7, wherein the prosthesis comprises a graft and at least one stent.

9. The introducer of claim 8, wherein the at least on stent comprises:
   a distal trunk stent portion expandable for deployment in a distal portion of the main lumen distal the branch lumen;
   a proximal trunk stent portion expandable for deployment in a proximal portion of the main lumen proximal the branch lumen; and
   at least one branch stent portion expandable for deployment in one of the branch lumens.

10. The introducer of claim 9, wherein the trunk deployment catheter comprises at least one inflatable deployment balloon for deploying the distal trunk stent portion and at least one inflatable deployment balloon for deploying the proximal trunk stent portion.

11. The introducer of claim 9, wherein the trunk deployment catheter consists of only a single inflatable deployment balloon maneuverable for deploying both the distal trunk stent portion and the proximal trunk stent portion.

12. The introducer of claim 9, wherein the distal trunk stent portion, the proximal trunk stent portion and each branch stent portion comprise separate stents.

13. A method for implanting a prosthesis in a distal location within a lumen from a proximal location outside the lumen, the distal location positioned at a junction of a main lumen and at least one branch lumen, the prosthesis comprising at least one stent and having a trunk and at least one arm, each arm for implantation into the branch lumen and the trunk for implantation into the main lumen, the method comprising the steps of:
   (a) providing an introducer comprising an outer sheath; an axial guide wire and at least one peripheral guide wire slidable within the outer sheath; a nose cone at a distal end of the outer sheath, the nose cone having an axial conduit slidable over the axial guide wire and at least one peripheral guide channel each for receiving one of the peripheral guide wires, each peripheral guide wire comprising an inflatable anchor balloon at a distal end thereof; a trunk deployment catheter concentric with the axial guidewire and having at least one inflatable deployment balloon; and at least one arm deployment catheter concentric with the peripheral guide wire and having at least one inflatable deployment balloon;
   (b) providing the prosthesis inside the outer sheath with the trunk mounted over the axial guide wire and at least one trunk stent portion mounted over each inflatable deployment balloon of the trunk deployment catheter and each arm mounted over one of the peripheral guide wires and at least one arm stent portion mounted over each inflatable deployment balloon of each arm deployment catheter;
   (c) introducing the introducer into the lumen until reaching an implantation position adjacent the branch lumen;
   (d) maintaining the introducer in the implantation position while advancing each peripheral guide wire distally through one of the peripheral channels of the nose cone until each wire is positioned at a sufficient depth within the corresponding branch lumen;
   (e) inflating each anchor balloon on each peripheral guide wire to fix the wire in a set position;
   (f) advancing the prosthesis over the axial and peripheral guide wires until each arm of the prosthesis is positioned at a sufficient depth within the branch lumen, and (g) inflating the deployment balloons to expand at least the trunk and arm stent portions of the prosthesis to implant the prosthesis.

14. The method of claim 13, wherein the main lumen comprises an aorta and the at least one branch lumen comprises the renal arteries, the prosthesis comprises two arms, the introducer comprises two peripheral guide wires and two arm deployment catheters, and the nose cone comprises two peripheral channels, the method further comprising implanting the prosthesis at the junction of the aorta and renal arteries.

15. The method of claim 14 comprising repairing an aneurysm by implanting the prosthesis.

16. The method of claim 13, wherein the prosthesis comprises a distal trunk stent portion distal the branch lumen and a proximal trunk stent portion proximal the branch lumen and implanting the prosthesis in step (g) comprises first inflating deployment balloons to deploy the distal trunk stent portion and all arm stent portions, then deflating each arm deployment balloon and retracting each arm deployment catheter at least to a position proximal the proximal trunk stent portion, then inflating a deployment balloon to deploy the proximal trunk stent portion.

17. The method of claim 16, wherein the trunk deployment catheter comprises a distal deployment balloon and a proximal deployment balloon, the method comprising inflating the distal deployment balloon prior to retracting the arm deployment catheters and inflating the proximal deployment balloon after retracting the arm deployment catheters.

18. The method of claim 16, wherein the trunk deployment catheter comprises a single trunk deployment balloon for expanding both the distal trunk stent portion and the proximal trunk stent portion, the method comprising inflating the single deployment balloon to expand the distal trunk stent portion, retracting the arm deployment catheters after expanding the arm stent portions, deflating and partially retracting the trunk deployment balloon to a position proximal the proximal trunk stent portion, and re-inflating the trunk deployment balloon to expand the proximal trunk stent portion.

19. The method of claim 16 wherein step (f) further comprises advancing the nose cone distal of the junction between the branch lumen and the main lumen.

20. A method for implanting a modular prosthesis in a distal location within a lumen from a proximal location outside the lumen, the distal location positioned at a junction of a main lumen and at least one branch lumen, the modular prosthesis comprising a trunk module for implantation into the main lumen and comprising at least one stent and at least one arm fitting, the modular prosthesis further comprising at least one arm module for implantation into the branch lumen, the arm module adapted to interconnect with the arm fitting of the trunk module and comprising at least one stent, the method comprising the steps of:

(a) positioning a first introducer in the main lumen in a first implantation position adjacent the branch lumen, the first introducer comprising an outer sheath; an axial guide wire slidable within the outer sheath; a nose cone at a distal end of the outer sheath, the nose cone having an axial conduit slidable over the axial guide wire; a trunk deployment catheter concentric with the axial guidewire and having at least one inflatable deployment balloon; the modular prosthesis inside the outer sheath with the trunk module mounted over the axial guide wire and at least one trunk stent portion mounted over each inflatable deployment balloon of the trunk deployment catheter (b) advancing the nose cone distally to a location distal of the junction of the main lumen with the branch lumen;

(c) implanting the trunk module with each arm fitting aligned with a corresponding branch lumen by inflating the trunk section deployment balloons to expand the trunk stent portions;

(d) positioning a second introducer in the main lumen in a second implantation position, the second introducer comprising an outer sheath; an axial guide wire and at least one peripheral guide wire slidable within the outer sheath; a nose cone at a distal end of the outer sheath, the nose cone having an axial conduit slidable over the axial guide wire and at least one peripheral guide channel each for receiving one of the peripheral guide wires, each peripheral wire comprising an inflatable anchor balloon at a distal end thereof; a trunk deployment catheter concentric with the axial guidewire and having at least one inflatable deployment balloon; at least one arm deployment catheter concentric with the peripheral guide wire and having at least one inflatable deployment balloon; each arm module mounted over one of the peripheral guide wires and at least one arm stent portion of each arm module mounted over each inflatable deployment balloon of each arm deployment catheter;

(e) maintaining the second introducer in the implantation position while advancing each peripheral guide wire distally through one of the peripheral channels of the nose cone and through one of the arm fittings in the implanted trunk module until each peripheral guide wire is positioned at a sufficient depth within the corresponding branch lumen;

(f) inflating each anchor balloon on each peripheral guide wire to fix the wire in a set position;

(g) advancing each arm module over one of the peripheral guide wires until each arm module is positioned at a sufficient depth within the branch lumen and in an interlocking position with one of the arm fittings of the trunk module;

(h) inflating each arm deployment balloon to expand at least the arm stent portions of each arm module to implant the arm module within the branch lumen and within the corresponding arm fitting of trunk module.

21. The method of claim 20 wherein the first introducer and the second introducer are the same introducer, and step (c) is performed with each arm module and arm deployment catheter positioned within the outer sheath proximal of the proximal end of the trunk module, and step (d) comprises retracting the nose cone to a position aligned with the branch lumen.

22. A method for implanting a prosthesis in a distal location within the lumen from a proximal location outside the lumen, the distal location positioned at a junction of a main lumen and at least one branch lumen, the prosthesis having a compressed configuration and an expanded configuration and comprising at least one portion for implantation into the branch lumen, the method comprising the steps of:

(a) providing an introducer comprising an outer sheath; an axial guide wire and at least one peripheral guide wire slidable within the outer sheath; a nose cone at a distal end of the outer sheath, the nose cone having an axial conduit slidable over the axial guide wire and at least one peripheral guide channel for receiving the peripheral guide wire, the peripheral wire comprising an inflatable anchor balloon at a distal end thereof;

(b) introducing the introducer into the lumen until reaching an implantation position adjacent the branch lumen;

(c) maintaining the introducer in the implantation position while advancing the peripheral guide wire distally through the peripheral channel of the nose cone until the peripheral guide wire is positioned at a sufficient depth the branch lumen;

(d) inflating the anchor balloon to fix the peripheral guide wire in a set position;

(e) advancing the prosthesis over the peripheral guide wire until at least a portion of the prosthesis is positioned at a sufficient depth within the branch lumen, and (f) expanding at least a portion of the prosthesis to implant the portion of the prosthesis in the branch lumen.

23. The method of claim 22 wherein the prosthesis is expanded in step (f) by balloon-expansion.

24. A prosthesis deployment system for deployment of a prosthesis in a lumen from a proximal location outside the lumen to a distal location within the lumen at a junction of a main lumen and at least one branch lumen, the system comprising:

an outer sheath having a distal end;

an axial guide wire slidable within the outer sheath;

at least one peripheral guide wire slidable within the outer sheath, the peripheral guide wire comprising an expandable balloon at a distal end thereof;

a nose cone located at the distal end of the outer sheath, the nose cone having a periphery, an axial conduit slidable over the axial guide wire, and at least one peripheral channel spaced apart from the axial conduit for receiving one of the peripheral guide wires; and a unitary prosthesis comprising a trunk section and at least one arm section extending radially from the trunk section.

25. The system of claim 24, wherein the prosthesis arm section is approximately perpendicular to the prosthesis trunk section.

26. The system of claim 24, wherein the prosthesis comprises two arm sections.

27. The system of claim 24, wherein the prosthesis is adapted to be deployed at a junction in which the main lumen comprises an aorta and each branch lumen comprises renal artery.

28. The system of claim 24, wherein the prosthesis comprises a graft and at least one stent.

29. The system of claim 28, wherein the at least one stent comprises:

a distal trunk stent portion expandable for deployment in a distal portion of the main lumen distal the branch lumen;

a proximal trunk stent portion expandable for deployment in a proximal portion of the main lumen proximal the branch lumen; and at least one branch stent portion expandable for deployment in one of the branch lumen.

30. The system of claim 29, wherein the distal trunk stent portion, the proximal trunk stent portion and each branch stent portion comprise separate stents.

31. An introducer for insertion in a lumen from a proximal location outside the lumen to a distal location within the lumen for deployment of a prosthesis at a junction of a main lumen and at least one branch lumen, the introducer comprising:

an outer sheath having a distal end;

an axial guide wire slidable within the outer sheath;

at least one peripheral guide wire slidable within the outer sheath;

a nose cone located at the distal end of the outer sheath, the nose cone having a periphery, an axial conduit slidable over the axial guide wire, and at least one peripheral channel spaced apart from the axial conduit for receiving one of the peripheral guide wires;

a trunk deployment catheter concentric with the axial guide wire and having at least one inflatable deployment balloon at a distal end thereof; and at least one peripheral deployment catheter, each concentric with one of the peripheral guide wires and having at least one inflatable deployment balloon at a distal end thereof.

* * * * *